United States Patent [19]
Ågerup

[11] Patent Number: 5,827,937
[45] Date of Patent: Oct. 27, 1998

[54] POLYSACCHARIDE GEL COMPOSITION

[75] Inventor: Bengt Ågerup, Upsala, Sweden

[73] Assignee: Q Med AB, Upsala, Sweden

[21] Appl. No.: 503,323

[22] Filed: Jul. 17, 1995

[51] Int. Cl.$^6$ .............................. C07H 1/00; C07H 13/02; A61K 31/715; A61K 31/73
[52] U.S. Cl. .................. 536/123.12; 536/20; 536/21; 536/119; 536/123.1; 536/124; 514/54; 514/55; 514/56
[58] Field of Search .................. 536/20, 21, 119, 536/123.1, 124, 123.12; 514/54, 55, 56

[56] References Cited

U.S. PATENT DOCUMENTS

| | | | |
|---|---|---|---|
| 4,197,846 | 4/1980 | Bucalo | 128/218 P |
| 4,716,154 | 12/1987 | Mälson et al. | 514/54 |
| 4,767,463 | 8/1988 | Brode et al. | 424/70 |
| 4,777,200 | 10/1988 | Dymond et al. | 524/458 |
| 4,803,075 | 2/1989 | Wallace | 424/423 |
| 4,863,907 | 9/1989 | Sakurai et al. | 514/56 |
| 4,963,666 | 10/1990 | Mälson | 536/55 |
| 5,007,940 | 4/1991 | Berg | 623/66 |
| 5,017,229 | 5/1991 | Burns et al. | 536/4.1 |
| 5,128,326 | 7/1992 | Balazs et al. | 514/54 |
| 5,143,724 | 9/1992 | Leshchiner et al. | 424/78.08 |
| 5,399,351 | 3/1995 | Leshchiner et al. | 424/422 |

FOREIGN PATENT DOCUMENTS

| | | |
|---|---|---|
| 0 161 887 | 11/1985 | European Pat. Off. . |
| 0203049 | 11/1986 | European Pat. Off. . |
| 0 265 116 | 4/1988 | European Pat. Off. . |
| 0 402 031 | 12/1990 | European Pat. Off. . |
| 0 466 300 | 1/1992 | European Pat. Off. . |
| 460 792 | 11/1989 | Sweden . |
| 2 205 848 | 12/1988 | United Kingdom . |
| WO 87/07898 | 12/1987 | WIPO . |
| WO 94/21299 | 9/1994 | WIPO . |

OTHER PUBLICATIONS

"Cross–Linked Gels of Hyaluronic Acid", Torvard C. Laurent et al., ACTA Chem. Scand., No. 1, p. 274, (1964).

*Primary Examiner*—John Kight
*Assistant Examiner*—Everett White
*Attorney, Agent, or Firm*—Burns, Doane, Swecker & Mathis, L.L.P.

[57] ABSTRACT

The present invention provides a process for preparing a cross-linked biocompatible polysaccharide gel composition, which comprises:

forming an aqueous solution of a water soluble, cross-linkable polysaccharide;

initiating a cross-linking of said polysaccharide in the presence of a polyfunctional cross-linking agent therefor;

sterically hindering the cross-linking reaction from being terminated before gelation occurs, an activated polysaccharide being obtained; and reintroducing sterically unhindered conditions for said activated polysaccharide so as to continue the cross-linking thereof to a viscoelastic gel. The invention also provides a gel composition obtainable by such a process as well as gel compositions for different medical uses.

35 Claims, No Drawings

POLYSACCHARIDE GEL COMPOSITION

TECHNICAL FIELD

The present invention relates to the field of biocompatible polysaccharide gel compositions, and more specifically to a novel process for cross-linking such compositions, a new gel structure thereby being obtained. The new structure imparts improved properties to the previously known gel compositions as well as enables new uses of said compositions, both as such and containing active ingredients.

BACKGROUND OF THE INVENTION

Water-binding gels are widely used in the biomedical field. They are generally prepared by chemical cross-linking of polymers to infinite networks. When using biocompatible polymers generally a low degree of cross-linking has to be utilized to maintain said biocompatibility. However, often a more dense gel is required to have a proper effect of the active ingredients utilized, and in such a case the biocompatibility will often go lost.

Another valuable property of water-binding gels, or hydrogels, is that peptides and larger biologically active substances can be enclosed therein to the formation of a sustained release composition. However, practical problems have been involved in accomplishing a sufficient maintenance time of the active ingredient, since generally the active ingredient is released at the same rate with which it was dissolved or enclosed in the composition referred to. Furthermore, if such a gel were densified in an attempt to maintain the active ingredient for a longer time, it would rapidly swell in an animal tissue where there is a free access of water.

One of the most widely used biocompatible polymers for medical use is hyaluronic acid. As it is present in identical composition in each living organism, it gives a minimum of reactions and allows for advanced medical uses. As a consequence thereof it has been the subject of many modification attempts. Thus, it has been cross-linked with agents such as aldehydes, epoxides, polyaziridyl compounds and divinylsulfone (Laurent et al, Acta Chem. Scand 18 (1964) No 1, p. 274; EP 0 161 887B1; EP 0 265 116A2; and U.S. Pat. No. 4,716,154).

In WO 87/07898 there is disclosed a reaction of a polysaccharide with a polyfunctional epoxide, removal of excess of said epoxide and finally drying operation to cross-link said polysaccharide into a film, powdered material or similar dry product. However, there is no suggestion therein to dilute the activated polysaccharide and then reconcentrate the same to the desired density or consistency which is then substantially permanent.

U.S. Pat. No. 5,128,326 discloses a number of modified hyaluronic acids for use as depot pharmaceuticals. The disclosed methods of "charging" the gel preparations are all based on a diffusion of the active ingredient into the gel and then a release thereof with the same diffusion constant. Contrary thereto the present invention involves a dissolution of the active ingredient followed by a densification or concentration of the gel composition until no or a very minor diffusion of said active ingredient takes place.

U.S. Pat. No. 5,399,351 discloses mixtures of gel and polymeric solutions, said solutions being utilized to improve the rheological properties of the gel. However, also in this case reversibly compressed gels are disclosed, as can be gathered from e.g. col. 6, lines 53–58.

SUMMARY OF THE INVENTION

According to the present invention it has unexpectedly been found that polysaccharide gel compositions having a novel structure and thereby new, outstanding properties can be obtained by using a new technique for the cross-linking thereof. Said new cross-linking technique enables a versatile control of the structure and properties of the manufactured polysaccharide gel composition, which in turn makes it possible to tailor the final composition for the intended purposes.

More specifically, one object of the present invention is to provide a process for preparing a cross-linked polysaccharide gel composition, the biocompatibility of which can be retained in spite of a high degree of cross-linking or polymerisation.

Another object of the invention is to provide a polysaccharide gel composition with viscoelastic properties in spite of being cross-linked to a substantial degree.

Yet another object of the invention is to provide a polysaccharide gel composition which is more or less irreversably densified or concentrated, i.e. which does not swell substantially or only to a limited degree when contacted with water.

Still another object of the invention is to provide a polysaccharide gel composition enclosing a biologically active substance for use as a sustained release composition or a depot composition.

Another object of the invention is to provide polysaccharide gel compositions containing a variety of biologically active substances for uses as medical or prophylactic compositions for different purposes.

Yet another object of the invention is to provide uses of the compositions referred to for the manufacture of medical or prophylactic compositions as well as for administration to mammals, especially humans.

Yet another object of the invention is to provide a partially cross-linked activated polysaccharide gel composition as obtained as an intermediate in the above-mentioned process according to the invention, which intermediate can be finally cross-linked in situ at any desired site.

These and further objects of the invention will become apparent by the more detailed description thereof presented below.

DETAILED DESCRIPTION OF THE INVENTION

According to one aspect of the present invention a process for preparing a cross-linked biocompatible polysaccharide gel composition is thus provided, which process comprises:

forming an aqueous solution of a water soluble, cross-linkable polysaccharide;

initiating a cross-linking of said polysaccharide in the presence of a polyfunctional cross-linking agent therefor;

sterically hindering the cross-linking reaction from being terminating before gelation occurs, an activated polysaccharide thereby being obtained; and reintroducing sterically unhindered conditions for said activated polysaccharide so as to continue the cross-linking thereof up to a viscoleastic gel.

In other words the new process according to the present invention involves a cross-linking of a water-soluble, cross-linkable polysaccharide in at least two steps or stages, where the cross-linking reaction is discontinued before the galation is initiated, said discontinuance being accomplished by sterically hindering said cross-linking reaction. The cross-linking reaction is then continued in a second step by reintroducing sterically unhindered conditions.

Thus, firstly is has unexpectedly been found that by said sterical hindrance an activated polysaccharide is obtained, the cross-linking or polymerization of which can be continued merely by reintroducing sterically unhindered conditions therefor. Secondly, it has also unexpectedly been found that the polysaccharide gel composition obtained thereby does not form the compact, dense structure which would have been obtained if performing the corresponding cross-linking reaction in one single step to a fully cross-linked gel but rather a viscoleastic gel. Furthermore, as was mentioned above, the new gel structure obtained by the present invention represents a substantially irreversible gel structure which does not swell to any appreciable extent in contact with water or any other aqueous medium. Generally this means that said reswelling is less than 10% by volume based on the volume as obtained from the process claimed.

Although the invention is not bound by any theory it may be that the new structure obtained by the present invention is a combination of cross-linking between existing polymer chains and an elongation of existing chains rather than a very dense network giving a very rigid structure. What may suggest such a mechanism is the fact that a viscoelastic product is obtainable by the invention.

As used herein the term "sterically hindering the cross-linking reaction" should be interpreted in a broad sense, i.e. it need not necessarily be a complete hinderance but in many cases rather a partial hindrance of the reaction referred to. That is, what is important is that the rate of cross-linking is substantially reduced to enable the final cross-linking reaction to take place with new reaction sites involved.

Similarly, the term "reintroducing sterically unhindered conditions" should also be interpreted broadly, which generally means that said sterically unhindered conditions need not necessarily be exactly the same sterical conditions as were used when initiating the cross-linking reaction. Thus, what is generally of importance is that said sterically unhindered conditions enable more rapid reactions to take place than said sterically hindered conditions.

The sterical hindrance of the cross-linking reaction should be obtainable in different ways, but a preferred embodiment of the invention in this respect is represented by the case where the sterical hindrance comprises diluting the aqueous medium in which the cross-linking reaction is performed, to accomplish a lower concentration of the polysaccharide in said medium.

To reintroduce sterically unhindered conditions should also be possible in different ways, but a preferred embodiment in this respect is the case which comprises evaporating the aqueous medium in which the cross-linking reaction is performed, to accomplish a higher concentration of the polysaccharide in said medium. Another preferred embodiment in this respect is represented by the case comprising dialysing the aqueous medium in which the cross-linking reaction is performed.

According to a preferred embodiment of the invention the sterical hindrance of the cross-linking reaction is accomplished before the cross-linking agent has been consumed. This in turn generally also means that the reintroduction of sterically unhindered conditions is initiated in the presence of said non-consumed cross-linking agent.

The sterical hindrance of the cross-linking reaction can generally be started or performed in the range of 50–90% of the total gelation time used in the process according to the invention, consideration also being taken to suitable elasticity or consistency for the intended use of the composition.

The inventive idea should be applicable to any biocompatible polysaccharide that is cross-linkable and soluble in an aqueous medium. Thus, the term "water soluble" should be interpreted in a broad sense, pure water not necessarily being necessary. That is, aqueous solution means any solution wherein water is the major component. A preferred sub-group of polysaccharides in connection with the invention is, however a glucose amine glucan, of which hyaluronic acid is a specially interesting example.

The cross-linking agent to be used in connection with the invention is any previously known cross-linking agent useful in connection with polysaccharides, consideration being taken to ensure that the biocompatibility prerequisites are fulfilled. Preferably, however, the cross-linking agent is selected from the group consisting of aldehydes, epoxides, polyaziridyl compounds, glycidyl ethers and dividylsulfones. Of these glycidyl ethers represent an especially preferred group, of which 1,4-butandiol digylcidylether can be referred to as a preferred example. In this connection it should also be mentioned that "polyfunctional" includes difunctional.

The initial cross-linking reaction in the presence of a polyfunctional cross-linking agent can be performed at varying pH values, primarily depending on whether ether or ester reactions should be promoted. Preferably this means that said cross-linking reaction is performed at an alkaline pH, especially above pH 9, e.g. in the range of pH 9–12, when promoting ether formations. When promoting ester formations said cross-linking reaction is preferably performed at an acidic pH, especially at pH 2–6.

One interesting aspect of the invention is represented by the case where the prepared cross-linked polysaccharide gel composition is utilized as such as the invention enables the manufacture of a viscoelastic composition. Such a viscoelastic composition is for instance useful in eye surgery, as a synovial fluid substitute, as eyedrops, etc, and as has been referred to above the present invention makes it possible to tailor the viscoelastic properties for such uses. Thus, by utilizing the sterical technology according to the present invention it is possible to obtain chain extensions, chain branchings, cross-links, etc, in a more controlled way that by the previously used techniques with more or less randomized coupling sites.

Furthermore, through the fact that the gels obtained in accordance with the invention do not retain their original volume in the presence of an aqueous medium, the new products do not cause any interfering or negative volume effects in these or other medical uses.

In accordance with the present invention it is also possible to include within the polysaccharide gel composition any biologically active substance for which a polysaccharide gel carrier is desired or accepted. In this context the dilution-concentration technique used in the process claimed enables the enclosure of said biologically active substance before subjecting the polysaccharide to sterically unhindered conditions. That is, while sterically unhindered conditions generally means a concentrating operation, such an operation means that the biologically active substance will be present in a phase that is more compacted than when said substance was included in said carrier. In other words the biologically active substance can be retained much longer as compared to previously known gel cross-linking reactions. Thereby a better sustained release profile for the active substance is obtainable.

In connection with the incorporation of the biologically active substance into the composition an adjustment of the conditions to physiological pH and salt conditions is preferably performed to have a preparation ready for medical use. Such a physiological adjustment is preferred also as concerns the reaction conditions as the second step of the process has been found to proceed well under suchg conditions.

The invention should not be limited in any respect as to the biologically active substance as compared to the use of said substance in prior cases. In other words the condition to be treated should be decisive for the specific substance to be selected.

However, interesting substances in connection with the invention can be selected from the group consisting of hormones, cytokines, vaccines, cells and tissue augmenting substances. Thus, the unique combination of properties of the new gel composition according to the present invention makes it extremely advantageous in connection with these substances, i.e. primarily thanks to outstanding depot or sustained release properties and non-swelling properties.

One interesting group of biologically active substances thus is tissue augmenting substances as a polysaccharide gel is an advantageous carrier therefor. Further details concerning such products can be found in WO94/21299. More specifically, a preferred tissue augmenting substance comprises a polymer selected from collagen, starch, dextranomer, polylactide and compolymers thereof, and poly-β-hydroxibutyrate and copolymers thereof.

In connection with hormones erytropoeitin and calcitonin are especially preferred.

The process according to the present invention also enables the incorporation of the biologically active substance by chemical reaction with the polysaccharide gel structure, or the cross-linking agent therefor, provided that said active substance contains functional groups reactive therewith. Unique properties or combinations of properties can thereby be obtained as in such a case for instance the release rate of the active ingredient will be decided by the degredation or decomposition of the polymer network rather than by the dissolution or migration rate for the substance referred to from the gel network.

A modification of last-mentioned technique in accordance with the invention means that the functional groups of the active substance may have been prereacted with a cross-linking agent for the polysaccharide. Preferably the same cross-linking agent is used as is used in the cross-linking of the polysaccharide.

Since the process of the present invention provides a new polysaccharide gel composition or structure, another aspect of the invention is represented by the novel polysaccharide gel composition prepared. In this respect the scope of protection encompasses not only the polysaccharide gel composition whenever prepared by said process but also any polysaccharide gel composition which is obtainable by a similar technique.

Expressed in another way the present invention also provides a cross-linked biocompatible polysaccharide gel composition, which is obtainable by cross-linking of a cross-linkable polysaccharide with a polyfunctional cross-linking agent therefor in two steps, the first cross-linking step being terminating before gelation occurs, by a sterical hindrance of the cross-linking reaction, and the second cross-linking step being initiated by reintroducing sterically unhindered conditions for said cross-linking reaction to continue the same up to a viscoelastic gel.

All those features which have been presented as preferred or interesting features in connection with the claimed process are applicable also to said polysaccharide gel composition per se and need not be repeated once more.

Still another aspect of the invention is represented by the case where an intermediate product is obtained by postponing the final step of the cross-linking reaction with sterically unhindered conditions to a later stage or site, for instance at the ultimate use of the composition. Thus, it has been found that the intermediate product obtained after the sterical hindrance of the cross-linking reaction possesses such a stability that the termination of the cross-linking reaction can be performed at a later stage.

The invention also relates to the composition defined above for use a medical or prophylactic composition.

Another aspect of the invention is the use of said composition for the manufacture of a medical or prophylactic composition for any of the above-mentioned specific medical or therapeutical purposes, tissue augmentation and hormone treatment of a mammal, especially a human being, being preferred applications.

Finally, the invention relates to a method of medical or prophylactic treatment of a mammal, especially a human being, which comprises administering a composition as defined above to a mammal in need of such a treatment.

EXAMPLES

The invention will now be exemplified by the following non-limiting examples.

Example 1

Activation of the polymer.

a. Under alkaline conditions

Polysaccharide in the form of 10 g of hyaluronic acid prepared by fermentation of Streptococcus were dissolved in 100 ml of 1% NaOH pH>9. Cross-linking agent in the form of 1,4-butandiol diglycidylether was added to a concentration of 0.2%. The solution was incubated at 40° C. for 4 hours.

b. Under acidic conditions

The experiment was performed as in 1a but at an acidic pH of about 2–6 by the addition of 1% of acetic acid to the solution instead of NaOH according to 1a.

Example 2

Preparation of a viscoelastic gel.

The incubates according to 1a and 1b were diluted to a volume which was twice the volume finally desired or about 0,5–1% and were neutralised. The gel was then rotary evaporated to a viscoelastic gel.

Example 3

Preparation of a gel containing dextranomer particles.

The incubates according to 1a and 1b were diluted to a strength of 1% and 20 g dry dextranomer particles (SEPHADEX®25, Pharmacia) were mixed with the solution, the particles being enclosed by the cross-linking of hyaluronic acid polymer in a few minutes as a consequence of the concentration of hyaluronic acid which is accomplished by an absorption of water by the dextranomer beads.

The viscoelastic gels obtained were stable, auto-clavable and injectable by means of thin hypodermic needles.

Example 4

Preparation of a gel for use as a depot medicine containing erytropoeitin (EPO).

The incubate obtained in Example 1a was diluted to a strength of 1% and the pH was adjusted by the addition of a citrate buffert according to the instructions from the

7 manufacturer (Ortho Biotech Inc., Raritan USA) for a good stability in aqueous solution. $5 \times 10^6$ IU of EPO were added under Stirring. After evaporating the solution to ¼ of the volume the polymer had been cross-linked to a depot composition and an amount of 20,000 IU of EPO/ml was recovered.

Example 5

Preparation of a gel for use as a depot preparation containing calcitonin.

Calcitonin from salmon 100 IU/ml (MIACALCIC® Sandoz) were admixed with 2% of polymer solution manufactured in accordance with Example 1b and the solution was concentrated to 5% (250 IU/ml) by rotary evaporation. A horse with chronic claudication in the right front leg was treated with an injection of 2 ml s.c. per week during two weeks. In the six weeks following thereafter said horse was free from pains. The serum calcium was lowered with 12% only.

Example 6

Preparation of a gel containing heparin to be released in a sustained way.

In a diluted activated polymer according to Example 4 heparin was dissolved in an amount of 5% of the polymer. The mixture obtained was equilibrated for 1 hour, whereupon it was evaporated to ¼ of the volume. A coagulation inhibiting release thereof was noted during 16 days of incubation in physiological saline.

Example 7

Preparation of a gel with covalently bonded heparin in a sterically controlled position.

Activated polymer according to Example 1 was precipitated in methanol under vigorous stirring. The fine threaded precipitation obtained was dried during the night. Heparin was activated in accordance with example 1. After said incubation (4 hours at 40° C.) the polymer precipitation was mixed with the activated heparin solution. The mixture was incubated during the night and the following day the gel solution was neutralised, particulated and washed from reactant residues.

The gel formed was able to bind growth factor, inter alia basic Fibroblast Growth Factor (bFGF), but did not show any inhibition of the coagulation of whole blood.

Example 8

Preparation of a gel containing positively charged groups of chitosan.

Incubation of a mixture of 7,5 g of hyaluronic acid polymer and 2,5 g of chitosan (See CURE® Protan) was performed in accordance with example 1. After a dissolution and a neutralisation a copolymerized viscoelastic solution was obtained. Said solution possessed healing promoting properties after having been applied to a sore slow in healing.

Example 9

Preparation of a gel which has been sterically coupled.

7,5 g of hyaluronic acid were activated in accordance with Example 1a. In the same way 2,5 g of dextran were activated. The hyaluronic acid was precipitated in methanol, the precipitation then being mixed with 500 ml of a diluted activated 0,5% dextran solution. After stirring and adjustment of pH and salt concentration a viscoelastic solution was obtained. 5 ml of said solution was infused in an Achilles tendon sheath which repeatedly showed inflammation in the form of soreness and "creaking". After four weeks said Achilles tendon problems had disappeared.

8

Example 10

Preparation of a gel for use as a medicinal depot containing GMCSF.

The product was prepared in accordance with Example 5 but instead of calcitonin there was added Granulocyte macrophage—colony stimulating factor, GMCSF (LEUCOMAX®) 1 mg/g polymer.

Example 11

Preparation of gel containing killed virus type Influenza A2.

The preparation was performed as in Example 4 but instead of EPO 40 960 HAU killed influenza horse virus per 100 ml of diluted active 1% polymer solution were added. After contraction 4× the preparation contained 1 600 HAU per ml. By a vaccination of more than 100 horses in connection with an epidemic influenza the preparation was found to be highly effective as to protection against infection, which protection was maintained for a long time (more than 6 months).

Example 12

Preparation of a fresh gel containing a living cell suspension.

A 5 ml fibroblast culture was mixed with 100 ml of a neutralized solution according to example 1a. The mixture was oxygenated and dried to half the volume. A viscoelastic solution containing living cells was obtained.

Example 13

Preparation of a dense micronised gel containing small peptides.

To an activated neutralized gel according to Example 1a there was added 5 mg of a peptide having 12 amino acids. The gel was evaporated during stirring to 10% and was suspended in mineral oil. After addition of methanol the dry gel particles were filtered off and washed clean from oil residues.

Example 14

Preparation of a gel containing the dense micronised gel with small peptides according to ExamDle 13.

To a 1% solution of neutralized polymer activated according to Example 1a microspheres from Example 13 were added. The gel was then evaporated to half its volume. A homogenous injectable and stable gel containing finely dispersed microspheres was formed.

Example 15

Preparation of a gel containing spherical polymethylmethacrylate (PMMA) beads having a size of 40–120 μm.

To 5 g of a polymer diluted to 1% and neutralized and activated according to Example 1a 100 mg of spheres of polymethylmethacrylate (PMMA) were added. Evaporation to 3% polymeric gel gave a stable injectable viscoelastic gel.

Example 16

Preparation of a gel containing PMMA fragments of 500 nm to which hydrophobic antigen has been added.

Haemagglutinin antigen prepared from A2 virus according to Example 11 was absorbed by hydrophobic interaction on 500 nm PMMA particles. Said particles were added to 1% solution according to Example 15 and a reduction to half the volume was accomplished. A stable homogenous viscoelastic gel was formed which was useful as a vaccine having a high adjuvant effect.

Example 17

A comparison between the degree of reswelling at free availability of water between conventionally prepared gels and gels prepared according to the present invention.

Hyaluronic acid gels prepared according to Laurent et al 1963 and according to Examples 1 and 2 above were dried to half their swelling volumes. Then they were reintroduced into their original solutions. The previously known gels swelled to their original volume while the gel compositions according to the present Examples 1 and 2 swelled marginally only (10%).

Example 18

Comparison between biological activity of EPO copolymerized with hyaluronic acid to a gel and the gel according to Example 1 into which EPO had been enclosed by a concentration of said gel.

Four patients under treatment with EPREX® (CILAG) erythropoietin for their anaemia caused by chronic uraemia were treated for two months with a dose each month according to the following regimen:

|  | Patient no. | | | |
| --- | --- | --- | --- | --- |
|  | 1 | 2 | 3 | 4 |
| Dose IU | 60 000 | 70 000 | 70 000 | 50 000 |
| Month 1 | Directly gelled depot, | Directly gelled depot, | Control | Control |
| Month 2 | Control | Control | Concentrated | Concentrated |

Directly gelled depot: Epoxide cross-linking under mild conditions according to Example 11 in the presence of EPO.
Control: EPO dissolved in 4% hyaluronic acid MW about $6 \times 10^6$ from cock's comb prepared according to U.S. Pat. No. 4,141,973 (HEALON® Pharmacia).
Concentrated: EPO enclosed within activated gel which was gelled through concentration.

The dose was selected as the total dose per month which was normally required by the patient to maintain the haemoglobin level. The serum level of EPO was analysed at regular Intervals by means of an immunochemical method.

Results

A common method of expressing the functionary effect of depot preparations is to calculate the curve area (units of EPO×days). This study also gives the bioavailability in the form of haemoglobin level in blood as 0=retained, += increased and -= reduced.

TABLE

|  | Patient no./month | | | | | | | |
| --- | --- | --- | --- | --- | --- | --- | --- | --- |
|  | 1/1 | 1/2 | 2/1 | 2/2 | 3/1 | 3/2 | 4/1 | 4/2 |
| Area under the curve | 41 | 424 | 57 | 534 | 224 | 952 | 567 | 656 |
| Haemoglobin control | − | + | − | + | 0 | + | + | + |

Conclusion

An enclosure of EPO in a contracted depot gives the highest possible release during the analysis. Attempts to perform the gelling reaction In the presence of EPO destroyed the hormones such that a very low release could be registered.

I claim:

1. A process for preparing a cross-linked biocompatible polysaccharide gel composition, which process comprises the following steps:
   (i) forming an aqueous solution of a water soluble, cross-linkable polysaccharide;
   (ii) initiating a first cross-linking reaction whereby cross-linking of said polysaccharide is effected using a polyfunctional cross-linking agent therefor;
   (iii) sterically hindering the first cross-linking reaction such that it is terminated before gelation occurs, resulting in the production of an activated polysaccharide; and
   (iv) performing a second cross-linking reaction after sterically unhindered conditions are reintroduced for said activated polysaccharide to produce a viscoelastic gel.

2. A process according to claim 1, wherein the polysaccharide is selected from the group consisting of glucose amino glucans.

3. A process according to claim 2, wherein said glucose amine glucan comprises hyaluronic acid.

4. A process according to claim 1 wherein the cross-linking agent is selected from the group consisting of aldehydes, epoxides, polyaziridyl compounds, glycidyl ethers and divinyl sulphones.

5. A process according to claim 4, wherein said glycidyl ether comprises 1,4-butanediol diglycidylether.

6. A process according to claim 1, wherein said sterically hindering of the cross-linking reaction comprises diluting the aqueous medium in which the cross-linking reaction is performed, to accomplish a lower concentration of the polysaccharide in said medium.

7. A process according to claim 1, wherein said reintroduction of sterically unhindered conditions comprises evaporating the aqueous medium in which the cross-linking reaction is performed, to accomplish a higher concentration of the polysaccharide in said medium.

8. A process according to claim 1, wherein said reintroduction of sterically unhindered conditions comprises dialysing the aqueous medium in which the cross-linking reaction is performed.

9. A process according to claim 1, wherein the initial cross-linking reaction in the presence of a polyfunctional cross-linking agent is performed at an alkaline pH, ether cross-linking reactions thereby being promoted.

10. The process of claim 9, wherein the cross-linking is effected at a pH above pH 9.

11. A process according to claim 1, wherein the initial cross-linking reaction in the presence of a polyfunctional cross-linking agent is performed at an acidic pH, ester cross-linking reactions thereby being promoted.

12. A process according to claim 1, wherein said sterical hindrance of the cross-linking reaction is accomplished before said cross-linking agent has been consumed.

13. A process according to claim 1, wherein a biologically active substance is enclosed within the cross-linked polysaccharide gel composition during the preparation thereof.

14. A process according to claim 13, wherein said active substance is enclosed within the gel composition by dissolving or dispersing the same in said activated polysaccharide before subjecting last-mentioned polysaccharide to sterically unhindered conditions.

15. A process according to claim 14, wherein said biologically active substance is selected from the group consisting of hormones, cytokines, vaccines, cells and tissue augmenting substances.

16. A process according to claim 13, wherein said biologically active substance is selected from the group consisting of hormones, cytokines, vaccines, cells and tissue augmenting substances.

17. A process according to claim 16, wherein said tissue augmenting substance comprises a polymer selected from the group consisting of collagen, starch, dextranomer, polylactide, poly-β-hydroxybutyrate and copolymers thereof.

18. A process according to claim 16, wherein said hormone is selected from the group consisting of erytropoeitin and calcitonin.

19. A process according to claim 13, wherein said biologically active substance contains functional groups reactive with the polysaccharide and is enclosed within the gel structure by chemical reaction therewith.

20. A process according to claim 19, wherein said biologically active substance containing functional groups has been prereacted with a cross-linking agent for said polysaccharide.

21. The process of claim 20, wherein the same cross-linking agent is used for said prereaction.

22. The process of claim 13, wherein the cross-linking is effected at a pH ranging from 2 to 6.

23. The process of claim 13, wherein the biologically active substance is introduced at physiological pH and salt concentration conditions.

24. A cross-linked biocompatible polysaccharide gel composition, which is obtainable by cross-linking of a cross-linkable polysaccharide with a polyfunctional cross-linking agent therefor in two steps, the first cross-linking step being terminated before gelation occurs by a sterical hindrance of the cross-linking reaction, and the second cross-linking step being initiated by reintroducing sterically unhindered conditions for said cross-linking reaction to continue the same up to a viscoelastic gel, wherein said gel composition exhibits retained biocompatibility, viscoelasticity and does not swell substantially when placed in contact with water.

25. A cross-linked biocompatible polysaccharide according to claim 24, which comprises a biologically active substance enclosed therein.

26. A composition according to claim 25, which is adapted as a depot preparation.

27. An improved method of medical or prophylactic treatment of a mammal, which comprises administration of a biologically active substance wherein the improvement comprises administering a composition as defined in claim 26 to a mammal in need of such a treatment.

28. The method of claim 27, which comprises treatment of a human being.

29. An improved method of medical or prophylactic treatment of a mammal, which comprises administration of a biologically active substance wherein the improvement comprises administering a composition as defined in claim 25 to a mammal in need of such a treatment.

30. The method of claim 29, which comprises treatment of a human being.

31. A method of treatment or prophylaxis of tissue augmentation in a mammal comprising administering a medical or prophylactic composition comprising a polysaccharide gel composition according to claim 25.

32. The method of claim 31, wherein the mammal is a human being.

33. A medical or prophylactic composition comprising a polysaccharide gel composition according to claim 24.

34. A method of hormone treatment of a mammal which comprises the administration of a medical or prophylactic depot composition comprising a polysaccharide gel composition according to claim 24, which contains a prophylactically or therapeutically effective amount of a hormone.

35. The method of claim 34, wherein the mammal is a human being.

* * * * *